US008485458B2

(12) United States Patent
Camprasse et al.

(10) Patent No.: US 8,485,458 B2
(45) Date of Patent: Jul. 16, 2013

(54) PROCESS FOR THE PREPARATION OF NACRE MECHANO-STRUCTURED BY MECHANOSYNTHESIS, MECHANO-STRUCTURED NACRE THUS OBTAINED AND USES THEREOF

(75) Inventors: Serge Camprasse, La Fleche (FR); Georges Camprasse, Paris (FR)

(73) Assignee: JD Invest, Saint Maur des Fosses (FR)

( * ) Notice: Subject to any disclaimer, the term of this patent is extended or adjusted under 35 U.S.C. 154(b) by 436 days.

(21) Appl. No.: 12/816,624

(22) Filed: Jun. 16, 2010

(65) Prior Publication Data

US 2011/0004218 A1    Jan. 6, 2011

(30) Foreign Application Priority Data

Jun. 17, 2009    (FR) ...................... 09 54066

(51) Int. Cl.
*B02C 17/00* (2006.01)
(52) U.S. Cl.
USPC ................. 241/23; 241/29; 241/30; 241/175; 241/184
(58) Field of Classification Search
USPC ................. 241/29, 30, 184, 23, 175
See application file for complete search history.

(56) References Cited

FOREIGN PATENT DOCUMENTS

| CN | 101062060 A | 10/2007 |
|---|---|---|
| FR | 2647334 A1 | 11/1990 |
| FR | 2777190 A1 | 10/1999 |
| FR | 2827478 A1 | 1/2003 |
| WO | 0184963 A1 | 11/2001 |

OTHER PUBLICATIONS

Q.L. Feng, F.Z. Cui, G. Pu, R.Z. Wang, H.D. Li "Crystal orientation, toughening mechanisms and a mimic of nacre" Materials Science and Engineering C 11 2000. 19-25.*
Lemos A Fetal: "Hydroxyapatite nano-powders produced hydrothermally from nacreous material", Journal of the European Ceramic Society, Jan. 1, 2006, pp. 3639-3646, vol. 26, No. 16, Elsevier Science Publishers, Barking, Essex, GB, XP024960271.
Database WPI Week 200825 Thomson Scientific, London, GB; AN 2008-D29692, XP002565641.
Gao et al: "Effect of nanometer pearl powder on calcium absorption and utilization in rats", Food Chemistry, Dec. 25, 2007, pp. 493-498, vol. 109, No. 3, Elsevier Ltd, NL, XP022534617.
Keith J et al: "Comparative analysis of macromolecules in mollusc shells", Comparative Biochemistry and Physiology.B. Comparativebiochemistry,Jan. 1, 1993, pp. 487-496, Pergamon Press, London, GB, vol. 105B, No. 3/04, XP002089924.
French Search Report in Corresponding Application No. FR 0954066 Dated Jan. 28, 2010.

* cited by examiner

*Primary Examiner* — Mark Rosenbaum
(74) *Attorney, Agent, or Firm* — Young & Thompson

(57) ABSTRACT

The present invention relates to a method for the preparation of mechano-structured nacre by mechanosynthesis of micrometric nacre powder, characterized in that the temperature of the nacre is kept below 40° C. It also relates to the mechano-structured nacre and to uses thereof, in particular on implants and bone substitute pieces on which the mechano-structured nacre is deposited.

14 Claims, 2 Drawing Sheets

PROCESS FOR THE PREPARATION OF NACRE MECHANO-STRUCTURED BY MECHANOSYNTHESIS, MECHANO-STRUCTURED NACRE THUS OBTAINED AND USES THEREOF

TECHNICAL FIELD

The present invention relates to a process for the preparation of mechano-structured nacre by mechanosynthesis. It also relates to the uses of this nacre, in particular as coating applied to implants, metal prostheses or bone filling pieces.

STATE OF THE ART

Nacre is an organomineral complex secreted by certain molluscs throughout their lives. It is mainly composed of crystallized calcium carbonate in the form of very pure aragonite arranged in superimposed layers, separated by layers of organic matter. The assembly of these mineral and organic parts shows the complexity of its composition.

In order to better understand the reasons which make nacre so special, certain biological molecules of the outer and inner shells of bivalve marine molluscs have been identified in patent WO9952940. For this purpose, powder was prepared from the outer and inner shell of *Tridacnae gigas* and of *Pinctada maxima* by cutting out fragments of shell measuring a few $cm^2$ then grinding them for two 3-minute phases in a planetary mill. The powder obtained had a grain size of between 300 and 500 microns. The active principles or marine biopolymers contained in the nacre were then extracted by cold hydrolysis, supercentrifugation and tangential ultra-filtration. Although this extraction method does not guarantee that all the components are effectively retained, they have identified proteins of the structural type constitutive of the extra-cellular matrix, such as essential amino acids, type I, II and III collagen (fibrous glycoproteins which are very abundant in the organic matter), elastin, glycosaminoglycanes and proteoglycanes. They have also demonstrated the presence of pro-factors and growth factors such as BMP, TGFβ and IGFII, cytokines, lipids and hexoses (C6 reducing sugars which are essential to cell metabolism), melanin compounds and carotenoids as well as mineral and metallic elements which are free or bound to specific biological molecules in order to form metalloproteins, metalloenzymes, porphyrinic and non-porphyrinic chromo-proteins, forming ⅔ of the constituent elements of organic matrix.

Numerous studies and records of clinical observations have not only shown the excellent biocompatibility of the marine biopolymers, but also all their pharmacological properties in the indications where they have been used. Thus, the power of skin regeneration and also of regeneration of both spongy and compact bone, in vivo and in vitro, of nacre has been demonstrated. Its specific composition and particular structure give compact nacre its histocompatible and non-biodegradable character but also constant mechanical properties comparable to those of natural tooth, human bone and the most resistant ceramics. Thus, the physico-chemical composition of nacre makes it the most suitable biomaterial for endosseous implantation in the compact form, as described in the patent FR2647334 proposing the use of nacre in bone substitute and radicular dental parts but also in powder form in other applications such as the cicatrization of losses of cutaneous and muscular substances and in the filling of losses of osseous substances.

However, the nacre from these molluscs used in compact form as endosseous implants, osteosynthesis plates and screws or bone substitute pieces, due to the low porosity of its surface only (Académie des Sciences publications, Clinical Material) with non-communicating pores, allows only a limited release of the osteoinductive active principles responsible for osteogenesis.

A need therefore exists for improvement or optimization of the properties of the nacre or also, a need to endow it with new properties allowing new applications.

The aragonitic nacre from the shell of bivalves, such as *Pinctada maxima* or other *pinctadas* and *Tridacnae gigas*, possesses a crystalline microstructure comparable to that of a natural nano-composite. In fact, the elementary component of nacre is a biogenic, organomineral and aragonitic crystal which is associated with and linked to other biocrystals by the organic matter resulting from the glycoprotein synthesis of specialized cells. These biocrystals are surrounded and separated by nanostructured organic matter made up of fibrils with sizes ranging from to 100 nanometres according to whether they are intercrystalline or interlamellar.

Given the intrinsic properties of the bio-polymers contained in the nacre of the molluscs mentioned previously, the presence of minerals and above all of metals that are free or bound to protein molecules such as the metalloproteins, metalloenzymes and metalloporphyrins, the present inventors then envisaged, in order to optimize the properties of the nacre, transforming it by mechanosynthesis into mechano-structured nacre particles.

They thus found that it was possible to obtain mechano-structured nacre by a process of mechanosynthesis.

DISCLOSURE OF THE INVENTION

Thus, a subject of the invention is a process for the preparation of mechano-structured nacre by mechanosynthesis. A further subject is the use of this mechano-structured nacre in the medical, veterinary or cosmetic fields and in particular in the design of bone or dental prostheses.

The most important attributes defining the characteristics of the nanoparticles are their size. In fact, the materials having particle sizes of the order of a nanometre have the characteristic of having particular physico-chemical properties pertaining to infinitesimal dimensions. Thus, the properties of the material can become changed and/or accentuated when the size of the particles comes close to a nanometre, for example, their chemical reaction surface is greater and the small size of the nanoparticles makes it easier for them to cross biological barriers. If appropriate, the pharmacological effects can be increased. The particles can therefore act within the cell, crossing the plasma membranes both over the cytoskeleton and over the organelles.

In this way all the pharmacological, biological and biochemical properties of a substance containing nanoparticles can be enhanced.

To these advantages linked to the size of the particles are added the advantages linked to the process of mechanosynthesis implemented in the invention. In fact, without wishing to be bound by any theory, the inventors are of the opinion that, due in particular to the presence of metalloproteins and metalloporphyrins and metalloenzymes in the nacre, a reorganization of the different constitutive elements among themselves is achieved during mechanosynthesis, a reorganization which is not obtained with standard grinding.

In particular, given the presence of free metals or bound metals involved in the molecular composition of the nacre test, i.e. the inner shell of the bivalve mollusc, in particular Mn, Cl, Cu, K, Sr, Na, Zn, Br, Ce, Fe, La, Sm and given their roles as coenzymes in all biological systems, in the catalytic reactions of hydrolysis and electron transfer in electron-transfer metalloproteins, transfer and activation of dioxygens, catalytic metalloenzymes, the inventors are of the opinion that the use of a top-down bioinorganic chemical process can endow all these elements with enhanced properties, creating from the assembly a new biocomposite exhibiting improved properties of tissue and cell regeneration.

The present inventors have discovered that keeping the nacre at a temperature below 40° C., preferably below 20° C., and even more preferentially below or equal to 0° C. during the process of preparation by mechanosynthesis made it possible to obtain mechano-structured nacre exhibiting improved properties and retaining all of its protein constituents.

DESCRIPTION OF THE INVENTION

Thus, a subject of the present invention is a process for the preparation of mechano-structured nacre by mechanosynthesis of micrometric nacre powder, characterized in that the temperature of the nacre is kept below 40° C., preferably below 20° C., and even more preferentially below or equal to 0° C. In the present Application and in what follows, the prefix "nano" will be used to describe particles the mean volume diameter of which is less than 500 nanometres, preferably less than 250 nm, and more preferentially less than or equal to 100 nm. Consequently, the terms "nanoparticles" and "nanonized particles" will be used to describe particles the mean volume diameter of which is less than 500 nanometres, preferably less than 250 nm, and more preferentially less than or equal to 100 nm. By "micrometric powder" is meant a powder having particles the mean volume diameter of which is comprised between 1 and 500 μm, preferably between 1 and 100 μm and more preferentially between 1 and 20 μm.

Furthermore, the terms "nacre particles to be treated" or "nacre powder to be treated" must be considered as relating to the nacre particles or to the nacre powder as they are before the application of the process of mechanosynthesis. Similarly, the terms "mechano-structured nacre particles" or "mechano-structured nacre" or "mechanically-induced nacre" will refer to the nacre powder processed according to the invention.

The mean equivalent volume diameter of the powders of the invention is determined by laser diffraction using a laser granulometer. The mean equivalent volume diameter or D(4; 3) is calculated from the grain size distribution measured over a wide range, according to the following formula: $D(4;3) = \Sigma(d^4)/\Sigma(d^3)$ Mechanosynthesis (or synthesis by mechanical route) is a mechanical method which consists of grinding micrometric powders, making it possible, under the effect of a succession of mechanical impacts on the particles inside a container, to obtain modified materials in the form of powder of nanometric size.

The mean volume diameter of the nacre powder obtained by the process of mechanosynthesis is less than 500 nm, preferably less than 250 nm and more preferentially less than or equal to 100 nm.

It is known that in bioinorganic chemistry, the grinding and the co-grinding achieved by the movement of grinding beads in an enclosed space itself subjected to significant acceleration forces applied to powdery metallic materials of different kinds lead to the production of nanoparticles and to the synthesis of new compounds with new properties by the implementation of chemical reactions induced by the high mechanical energy caused by the type of grinding implemented.

The metallic elements present in the organic matter of *Pinctada maxima* or other *Pinctadas* and of *Tridacnae gigas* such as: Sm, La, Zn, Br, Ce, Fe, Mn, Cu, K, Sr, Na and Ca in the free form or bound to enzymatic and non-enzymatic proteins, with porphyrins, make the aragonite of these molluscs a particular and unique biological system suitable for use in bioinorganic or biomimetic chemistry, a discipline studying the dynamics of the metal cations in biological systems.

It can therefore be seen that all the metal ions contained in the organic matter of the aragonite of *Pinctada maxima* and other *Pinctadas* and of *Tridacnae gigas* have a determining role in cell metabolism at all levels: ion channels, concentration of the cellular metal cations, hydrolysis reactions, regeneration of the cytoskeleton, electron transfer, transport and activation of the dioxygen, inhibition of the oxidative stress playing a major role in cell and tissue homeostasis.

The use of a planetary mill with decoupled parameters is particularly well suited to the synthesis of nanomaterials by mechanical routes. The planetary mill is constituted by a central turntable on which satellites are fixed, the centrifugal acceleration being controllable as a function of the relative conditions of rotation of the turntable and of the satellites.

As nacre is a very hard material, it is important that, during the grinding, no particle originating from the mill or beads contaminates the nacre powder thus obtained. This is why the grinding bowl or bowls as well as the grinding beads used according to the invention must be constituted by a material which is harder than the nacre, biocompatible and non-polluting. There may be mentioned as material, for example, zirconium oxide or a zirconium-yttrium alloy, these materials will not release chemical elements during violent and repeated impacts with the nacre in the grinder.

In the process of the invention, a nacre powder to be treated, having an average volume diameter comprised between 1 and 20 microns, is preferentially used in order to limit the duration and the number of grinding cycles.

According to the process of the invention, the nacreous test (i.e. the inner shell of the bivalve) of the shell is crushed then ground. The use of such a process makes it possible to preserve and treat all of the organic matter linked to the biogenic calcium carbonate crystals. Without wishing to be bound by any theory, the present inventors are of the opinion that the process of mechanosynthesis in the planetary mill allows the grinding of all the organic and metallic elements of the biomaterial, and causes the tearing, crushing, cohesion, and loss of cohesion, plastic and elastic deformation of the different nanoparticles by inducing the synthesis of new molecules where the metalloproteins, metalloenzymes and metalloporphyrins are aggregated either with each other via their prosthetic groups, or with other proteins or also with other free metal ions, creating new amino acid sequences giving rise to oligopeptides, polypeptides, peptides or proteins provided with new physico-chemical and biological properties.

The inner shell is used as it is, it is crushed and ground, and not subjected to any preliminary treatment, except for decontamination in particular with bleach (hypochlorite), or other decontaminant, for example a quaternary ammonium, calbenium, then rinsing with water.

The nacre utilized in the process of the invention is obtained from the nacre test of the shell of bivalves chosen from the group comprising *Pinctada maxima, Pinctada margaritifera* or other *Pinctadas, Tridacnae gigas*, and mixtures thereof.

According to a particular embodiment, the invention relates to a process for the preparation of mechano-structured nacre by mechanosynthesis of micrometric nacre powder comprising the following successive stages:

a) the nacre powder to be treated is placed in a grinding bowl of a planetary mill, then b) $N_i$ grinding beads (with i an integer comprised between 1 and 20, preferably between 3 and 15 and more preferentially between 5 and 14; $N_i$ is an integer comprised between 2 and 150, preferably between 10 and 100 and more preferentially between 20 and 85) of diameter $D_i$ are placed in the grinding bowl, c) the planetary mill is started up at a rotational speed V comprised between 800 and 1400 rpm, preferentially at 1100 rpm, with an acceleration of 90 to 110 G, preferably of 90 to 100 G and more preferentially of 95 G.

d) the planetary mill is stopped and the grinding beads of diameter $D_i$ are removed, Stages b, c and d are repeated with $N_{i+1}$ (with $N_{i+1} > N_i$) grinding beads of diameter $D_{i+1}$ (with $D_{i+1} < D_i$), until nacre particles of the desired size are obtained;

when the desired size of the particles is obtained, on completion of stage d), the mechano-structured nacre is recovered.

Thus, the choice of the number of grinding cycles will depend on the desired particle size. The diameter of the beads is comprised between 1 and 30 mm; preferably between 1 and 10 mm and more preferentially between 1 and 5 mm. The number and diameter of the beads will depend on the size of the grinding bowl. For example, with a grinding bowl having a volume of 500 ml, it is possible to envisage the use of 25 beads 20 mm in diameter, or 50 beads 10 mm in diameter or also 80 beads 5 mm in diameter.

According to a particularly preferred embodiment, the number of beads and their diameter are such there will be a ratio of 2/5 by weight of nacre particles to be treated to 3/5 by weight of beads. This proportion is perfectly suited to grinding in a grinding bowl the useful volume of which is 500 mL.

By useful volume is meant the capacity of the empty and closed grinding bowl.

Furthermore, the smaller the diameter of the beads, the greater the number of impacts and the more rapid the mechanosynthesis.

According to an advantageous embodiment, beads 2 mm in diameter are used.

Maintaining the nacre at a temperature below 40° C., preferably below 20° C., and even more preferentially below or equal to 0° C., throughout the entire process of mechanosynthesis is necessary for the non-alteration of the tertiary structure of the organic elements and in particular of the proteins composing the nacre.

Thus, according to a particular embodiment of the invention, the grinding bowl, the nacre powder to be treated and/or the grinding beads are cooled down before use to a temperature comprised between −30° C. and 5° C., preferably between −20° C. and −15° C., and optionally before each repetition of stages b), c) and d).

The grinding bowl, the nacre powder to be treated and/or the grinding beads can thus be placed in a freezer at a temperature comprised between −30° C. and 5° C., preferably between −20° C. and −15° C. for a period of time ranging from 1 minute to 48 hours. More preferentially, the assembly comprising the grinding bowl, the nacre powder to be treated and/or the grinding beads is placed in a freezer at a temperature of −18° C. for 24 hours. Moreover, this preliminary cooling down makes it possible to increase the water content of the nacre and thus facilitate the grinding and the mechanosynthesis. The water content which is initially 0.5% relative humidity for the micronized nacre utilized as starting product, can increase to 5% relative humidity during the cooling cycles.

Similarly, the grinding of stage c) can be interspersed with cycles of cooling the grinding beads, the grinding bowl and/or of the nacre powder to be treated in order to limit the increase in temperature undergone by the nacre powder during the grinding.

Thus, according to a particular embodiment of the invention, the process of mechanosynthesis of nacre powder is characterized in that the grinding cycles c) are carried out under a cooled atmosphere or interspersed with cooling cycles.

It is also possible to provide the planetary mill with a ventilation device intended to counterbalance the exothermic reaction resulting from the high energy generated by the rotational speed of the assembly and by the high-speed impacts of the beads, or to carry out the process or at least stage c) under liquid nitrogen.

The mechano-structured nacre obtained on completion of the process of the invention can be sterilized, for example by gamma radiation at less than 25 kGy or with ethylene oxide for 24 hours followed by 24 hours' aeration.

According to another particular embodiment of the invention, the process of mechanosynthesis of nacre particles is characterized in that:

the nacre powder to be treated is placed in a grinding bowl, grinding beads are placed in the grinding bowl and the assembly comprising the nacre powder to be treated, the grinding beads and the grinding bowl are cooled down to a temperature comprised between −30° C. and 5° C., preferably between −20° C. and −15° C., the refrigerated nacre powder to be treated then undergoes:

a) grinding cycles with grinding beads 10 mm in diameter until nacre particles having a mean volume diameter comprised between 5 and 15 microns are obtained, then b) grinding cycles with grinding beads 5 mm in diameter, until nacre particles having a mean volume diameter comprised between 800 nanometres and 2 microns are obtained, then c) grinding cycles with grinding beads 2 mm in diameter, until nacre particles having a mean volume diameter comprised between 0.01 and 500 nanometres, preferably between 0.01 and 250 nm and more preferentially between 0.01 and 100 nm are obtained, the mechano-structured nacre is then detached from the wall of the bowl and from the beads, sieved and recovered.

The grinding is carried out by cycles so as to limit the heating of the nacre.

According to another embodiment, a subject of the present invention is a process of mechanosynthesis of nacre particles characterized in that:

the nacre powder to be treated is placed in a grinding bowl, grinding beads are placed in the grinding bowl and the assembly comprising the nacre powder to be treated, the grinding beads and the grinding bowl is cooled down to a temperature comprised between −30° C. and 5° C., preferably between −20° C. and −15° C.,—the refrigerated nacre powder then undergoes:

a) 5 to 15, preferably 7 to 13 cycles, and even more preferentially 8 to 11 grinding cycles, each cycle lasting to 10 minutes, preferably 2 to 8 minutes and more preferentially 6 minutes, carried out with grinding beads 10 mm in diameter, then b) 5 to 15 grinding cycles, preferentially 10 cycles, of 1 to 10 minutes, preferentially 6 minutes, carried out with grinding beads 5 mm in diameter, then c) 5 to 15 grinding cycles, preferentially 10 cycles, of 1 to 10 minutes, preferentially 6 minutes, carried out with grinding beads 2 mm in diameter, the mechano-structured nacre is then detached from the wall of the bowl and from the beads, sieved and recovered.

According to a particularly preferred embodiment, the process of mechanosynthesis of nacre particles is characterized in that:

the nacre powder to be treated is placed in a grinding bowl, grinding beads 2 mm in diameter are placed in the grinding bowl and the assembly comprising the nacre powder to be treated, the grinding beads and the grinding bowl is cooled down to a temperature comprised between −30° C. and 5° C., preferably between −20° C. and −15° C.;

the refrigerated nacre powder then undergoes 20 5-minute grinding cycles with the grinding beads until nacre particles having an average volume grain size of less than 500 nm, preferably less than 250 nm and more preferentially less than or equal to 100 nm are obtained, after each cycle, the powder is detached from the wall of the bowls and sieved, then the powder, the bowls and the beads are frozen for 24 hours at a temperature comprised between −30° C. and 5° C., preferably between −20° C. and −15° C.;

after the last cycle, the mechano-structured nacre is then detached, sieved and recovered.

The invention also relates to mechano-structured nacre which can be obtained by the process described above and which has a mean volume diameter comprised between 0.01 and 500 nanometres, preferably between 0.01 and 250 nm and more preferentially between 0.01 and 100 nm.

The mechano-structured nacre obtained by the process of mechanosynthesis is characterized by X-ray diffraction, by Raman spectroscopy and by laser granulometry in order to access qualitative and quantitative information. The latter show, in random fashion, the presence of calcium carbonate in the crystalline form, as well as a very small quantity in the amorphous form which is explained by an increase in the pressure inside the bowl (approximately less than 10 GPa) for a short time.

According to an embodiment of the invention, the nacre powder to be treated is ground together with at least one material other than nacre.

This material other than nacre is chosen from the group comprising more than 90%-deacetylated chitosan powder, chitin, algae, insoluble and soluble biopolymers extracted from the nacreous test and from the outer shell of the above-mentioned bivalves, copper sulphate ($CuSO_4$, $5H_2O$), zinc oxide, gold or silver, and mixtures thereof. As copper sulphate, it is possible to use pentahydrated copper sulphate, crystallized or sublimed copper sulphate. There can be mentioned as a preferential example, the simultaneous grinding of nacre powder having a mean volume diameter comprised between 1 and 20 microns and of more than 90%-deacetylated chitosan powder with a mean volume diameter of approximately 150 microns and having a density of 0.6 g/cm$^3$. The simultaneous treatment of these two powders by the process of mechanosynthesis of the invention gives rise to a new mechano-structured biomaterial in which the three-dimensional form of the chitosan particles allows close cohesion with the mechano-induced aragonite biocrystals.

The mechano-structured nacre and/or the mechano-structured biomaterial according to the invention can be used in numerous applications, such as medical, veterinary or cosmetic applications. Thus, according to a particular embodiment of the invention, the mechano-structured biomaterial resulting from the simultaneous grinding of nacre powder and more than 90%-deacetylated chitosan powder obtained by the process according to the invention is included in the composition of cosmetic preparations, in particular for anti-ageing treatment, powder, treatment foundation, lipstick, nail-care products, deodorants and hair-care products.

The mechano-structured nacre and/or the mechano-structured biomaterial according to the invention can also be used in other fields such as the medical, pharmaceutical or veterinary fields, in particular in the formulation of eye lotion, ophthalmic gel and cream, optionally in combination with medicamentous substances such as antibiotics, anti-inflammatories and vasodilators.

Thus, preferentially, the mechano-structured nacre and/or the mechano-structured biomaterial according to the invention are used in dentistry, for example in bone filling, implantation, bone substitute pieces, or also for treating periodontal diseases and also as additives to polymerizable resins for the cosmetic crown restoration. Thus, for example, the mechano-structured nacre and/or the mechano-structured biomaterial obtained by the process according to the invention can be included in the composition of root-canal paste for endodontic treatments, pulp capping and cavity-liner cement. It can then be combined with components such as zinc oxide, calcium hydroxide, eugenol or any other essential oil.

A subject of the present invention is also an implant, comprising a core of structural material, optionally of nacre or a prosthetic element made of metal or other material, on the surface of which is deposited as a covering by sputtering, spraying, coating, electrolysis or immersion, mechano-structured nacre and/or mechano-structured biomaterial according to the invention.

This implant, or prosthetic element is of variable size and diameter and is characterized in that its entire surface is covered with mechano-structured nacre and/or a mechano-structured biomaterial, as described in the invention. The production of a covering from mechano-structured nacre and/or mechano-structured biomaterial thus makes it possible to endow it with new functionalities. In fact, given all of the properties of the mechano-induced nanoparticles, it becomes possible by surface treatment of a material, by spraying or coating with mechanically coated particles:

to modify its surface roughness for better keying, to increase its interface with the receiving site without modifying the shapes and dimensions thereof, in order to render immediately bioavailable all the molecules endowed with pharmacological properties that are involved in the regeneration and cicatrization processes and finally, to accelerate the biomaterial-cells interactivity, in order to facilitate the functional orientation of the cells and tissues of the receiving site as well as to increase its biocompatibility and its functionality.

In the remainder of the text, the terms "implant" or "prosthetic element" will be used indiscriminately.

The present invention therefore also relates to an implant preferentially made of nacre, characterized in that it is covered partially or over its entire surface with mechano-structured nacre and/or with mechano-structured biomaterial prepared according to the process of the invention, by a process allowing the deposition of mechano-induced nanoparticles, such as sputtering, spraying, coating, electrolysis or immersion.

Thus, according to a preferred embodiment of the invention, the mechano-structured nacre and/or the mechano-structured biomaterial are applied as a covering by sputtering, spraying, coating, electrolysis or immersion.

According to a particular aspect of the invention, the mechano-structured nacre and/or the mechano-structured biomaterial prepared according to the process of the invention is used in the coating of bone and dental implants, and bone substitute pieces.

The invention is better understood if reference is made to the examples and attached drawings which are non-limitative, in which FIGS. 1 to 3 represent two preferred embodiments of the invention:

Figure 1:
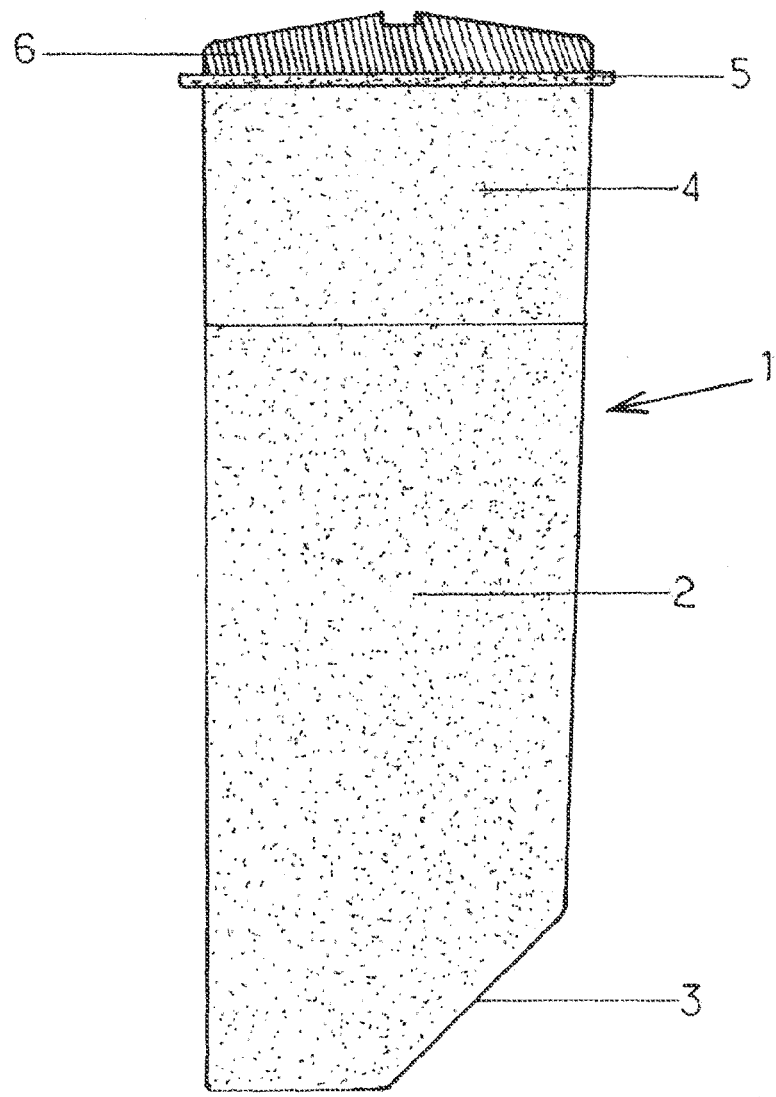
FIG. 1 represents a schematic view of an implant.

The implant (1) of FIG. 1 comprises a part in the general form of a cylinder (2), for example, of approximately 10 mm, the lower end of which is wedge-shaped (3). A superstructure made of polyoxymethylene marketed under the trademark Delrin® (4) is screwed onto the upper end of the implant, and comprises around its upper edge a ring made of polyester felt marketed under the trademark Dacron® (5) for example approximately 1 mm wide and 2 mm high. The superstructure (4) comprises in its centre a threaded orifice equipped with an obturator screw (6). The implant-obturator screw assembly is completely covered by sputtering, spraying, electrolysis or coating, with mechano-structured nacre prepared according to the process of the invention. However, only part of the implant shown in FIG. 1, in particular the part (2) and/or the part (4), can be covered. Coating can also be carried out with the mechano-structured biomaterial of the invention.

Figure 3:
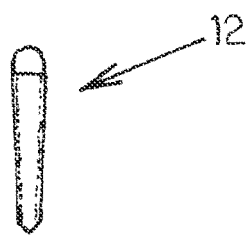
FIG. 3 represents the fastening screw of FIG. 2.
Figure 2:
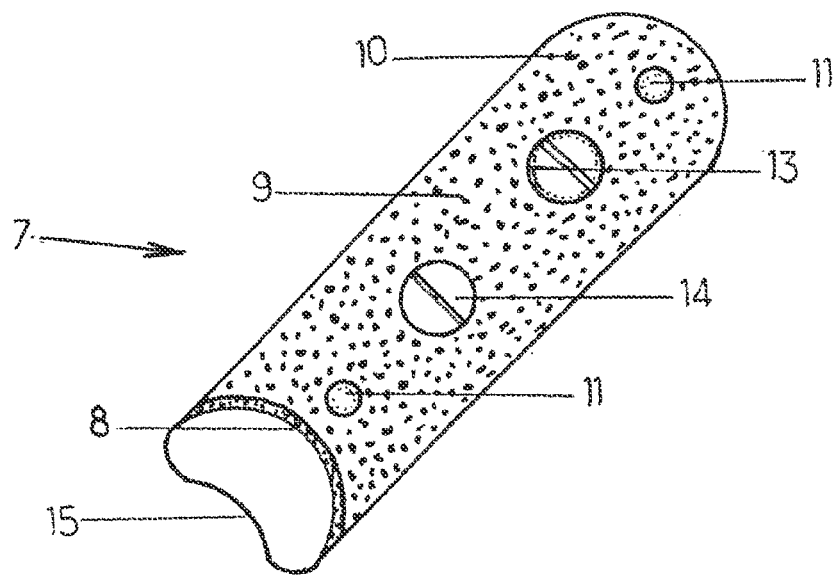
FIG. 2 represents a schematic view of a bone substitute piece.

According to another embodiment, the product according to the invention shown in FIGS. 2 and 3 is a bone substitute piece (7) intended to fill any loss of maxillary bone substance. The product has the general shape of a parallelepiped of variable dimensions the upper convex surface (8) of which is covered with a membrane made of polyester felt marketed under the trademark Dacron® (9) stopping at the level of the rounded edges of the parallelepiped (10). Its two ends are pierced by 2 threaded orifices (11), for example approximately 2 mm in diameter, intended to allow it to be fixed to the residual bone using two screws (12) (FIG. 3). These screws are of the same kind as the biomaterial of the implant. Depending on its length, the bone substitute piece is pierced by one or more threaded orifices (13), for example 4 mm in diameter, intended to receive a superstructure made of biocompatible synthetic material, for example made of polyoxymethylene marketed under the trademark Delrin® and provided with obturator screws (14). The superstructure is intended to support the prosthetic restoration element. Its lower concave surface (15) is intended to fit the surface of the residual bone. The bone substitute piece/fixing screw assembly is completely covered by sputtering, spraying, electrolysis, coating or mechano-structured nacre according to the invention. However, only part of the implant shown in FIG. 2 can be covered. Of course, the surface treatment can also be carried out with the mechano-structured biomaterial according to the invention.

Thus, a subject of the present invention is also a bone-filling piece comprising a core made of structural material, optionally made of nacre, on the surface of which is deposited, as a covering, by sputtering, spraying, coating, electrolysis or immersion, mechano-structured nacre and/or mechano-structured biomaterial according to the invention.

The product according to the invention can also be presented in the form of an osteosynthesis plate and screw made of structural material, preferentially made of nacre in compact form cut from the thickness of the shell, of variable dimensions also covered with mechano-structured nacre or with a mechano-structured biomaterial. The screws and plates cut from the nacre in compact form have physical characteristics such that the density, resilience, Vickers hardness, compressive resistance, elasticity modulus, are similar to those of bone. As a result, they do not need to be removed after constitution and remodelling of the callus and can therefore be kept in place permanently, thus avoiding any new surgical operation. The product according to the invention can also be compacted under high pressure in moulds of variable shape and dimension in order to produce bone substitute pieces intended to replace epiphyses, diaphyses and portions of the long bones or other parts of the skeleton.

It is to be noted that the implants produced according to the invention can be used in orthopaedic, maxillo-facial and odontostomatological surgery.

The invention can be used in mammals, in particular in humans.

EXAMPLES

The following examples illustrate the present invention.

Example 1

Micronized nacre powder to be treated is prepared according to the following process:
- the nacre test of *Pinctada maxima* is washed and decontaminated with 1% bleach then processed with a crusher and reduced to fragments of 10 mm to 1 cm,
- the product of crushing is then removed then placed in a zirconium oxide grinding bowl of a planetary mill,
- 15 zirconium oxide grinding beads 30 mm in diameter are each then placed in the grinding bowl,
- the planetary mill is then started up at a rotational speed of 400 rpm for 5 minutes, the device turning clockwise and anti-clockwise alternately,
- the product of crushing having undergone grinding is then sieved in a sieving machine 200 mm in diameter comprising 5 sieves of different sizes: 250 microns, 150 microns, 100 microns, 50 microns, 20 microns then a collecting base.

The nacre powder collected in the collecting base has a mean volume diameter of less than 20 microns.

Example 2

Mechano-structured nacre is prepared according to the following process:

a) the nacre powder to be treated obtained in Example 1 is placed in a grinding bowl of a planetary mill, b) 25 zirconium oxide beads 10 mm in diameter are added to the bowl, c) the assembly comprising the nacre powder to be treated, the grinding bowl, as well as the zirconium oxide beads is placed in a freezer at a temperature of −18° C. for 24 hours, d) the planetary mill is started up at a rotational speed of 1100 rpm for an acceleration of 95 G, for 10 cycles of 6 minutes each, separated every 2 cycles by 2 hours of freezing at −18° C., e) the planetary mill is stopped and the zirconium oxide beads 10 mm in diameter are removed. Stages b), c), d) and e) are repeated with 50 zirconium oxide beads 5 mm in diameter, then with 80 zirconium oxide beads 2 mm in diameter. The mechano-structured nacre is then detached from the wall of the bowl, sieved and recovered. It has a mean volume diameter of less than 150 nm. It is then sterilized by gamma radiation at 25 kGy.

Example 3

Mechano-structured nacre is prepared according to the following process:

a) Micronized aragonitic nacre powder with a mass of 200 grams obtained in Example 1 is placed in a grinding bowl with a capacity of 500 mL
b) Zirconium oxide beads with a diameter of 2 mm and a weight of 300 grams are added
c) The assembly comprising the micronized nacre powder, the bowl as well as the zirconium oxide beads is placed in a freezer at a temperature comprised between −15° C. and −20° C. for 24 hours
d) Once the bowls are put into place, the planetary mill is started up at a rotational speed of 1100 rpm for an acceleration of 95 G, for 20 cycles of 5 minutes each separated by two hours of freezing at a temperature comprised between −15° C. and −20° C.
e) At the end of each cycle, the powder is detached from the wall of the bowls and in the last cycle, the mechano-structured powder is detached and sieved in order to recover the beads The mechano-structured nacre is recovered, conditioned and sterilized by ionizing radiation or ethylene oxide vapour for 24 hours followed by 24 hours of aeration.

Example 4

A mechano-structured biomaterial resulting from a co-ground homogenate of nacre particles and chitosan is prepared according to the following process:
a) 200 g of the nacre powder to be treated obtained in Example 1 is placed in a grinding bowl with a capacity of 500 mL, of a planetary mill,
b) the more than 90%-deacetylated chitosan powder, having a mean volume diameter of approximately 150 μm and density of 0.6 g/cm$^3$ is added to the bowl,
c) 300 grams of zirconium oxide beads 2 mm in diameter are added to the bowl,
d) the assembly comprising the nacre powder to be treated, the deacetylated chitosan powder, the grinding bowl, as well as the zirconium oxide beads is placed in a freezer at a temperature of −18° C. for 24 hours,
e) the planetary mill is started up at a rotational speed of 1100 rpm for an acceleration of 95 G, for 10 cycles of 6 minutes each, separated every 2 cycles by 2 hours of freezing at −18° C.,
f) the planetary mill is stopped and the zirconium oxide beads 2 mm in diameter are removed.

Stages c), d), e) and f) are repeated until a co-ground homogenate of nacre and deacetylated chitosan is obtained, exhibiting an equivalent mean volume diameter of the order of a nanometre. The mechano-structured biomaterial is then detached, sieved and recovered. Then it is sterilized by gamma radiation at 25 kGy.

Example 5

Plates and screws are cut from the nacre mass which is recovered from the mechano-structured nacre obtained in Example 2. The plate and the two screws produced according to FIGS. 2 and 3 are then placed on the femur of a cull ewe. Radiological examination after one month shows that the plate and the screw have been covered by cortical bone and are completely integrated in the remoulded callus.

Example 6

A bone substitute is prepared, the composition of which per 100 g is as follows:

96 g of nacre having a mean volume diameter comprised between 20 and 350 microns,
4 g of mechano-structured nacre of Example 2,

Example 7

A sealing cement for hip, knee or shoulder prostheses is prepared. The composition of the sealing cement per 100 g is as follows:
90 g of nacre powder having an mean volume diameter of 5 to 50 microns,
10 g of mechano-structured nacre of Example 2.

Example 8

A gel or a paste is prepared, intended for the treatment of periodontal diseases in odontostomatology, the composition of which per 100 g is as follows:
5 g of nacre powder having an mean volume diameter between 5 μm and 10 μm,
4 g of mechano-structured nacre of Example 2,
0.05 g of chlorhexidine
2 g of xanthan gum,
demineralized water qsp 100 g

Example 9

A paste is prepared, which can be used for endodontic treatments, as cavity liner or in pulp capping, the composition of which per 100 g is as follows:
15 g of nacre powder having an mean volume diameter between 5 μm and 20 μm,
5 g of mechano-structured nacre of Example 2,
80 g of zinc oxide,
The mixture thus obtained can be mixed with eugenol or any other aqueous or oily vectors or any polymer which is biocompatible in order to produce a fluid paste for extemporaneous use for obturation of the root canals.

Example 10

A mixture which can be used for the obturation of defects in the enamel and dentine is prepared, the composition of which per 100 g is as follows:
80 g of photopolymerizable epoxy resin
10 g of silane coupling agent
10 g of mechano-structured nacre of Example 2

Example 11

A formulation intended for major burn therapy is prepared, the composition of which per 100 g is as follows:
7 g of nacre powder having an mean volume diameter comprised between 1 and 5 microns,
3 g of mechano-structured nacre of Example 2,
qsp 100 g of cold cream, alginate and chitosan.

Example 12

A cream or gel intended for the treatment of cutaneous, muscular or mucous membrane lesions, sores and ulcers is prepared, the composition of which per 100 g is as follows:
1.7 g of nacre powder having an mean volume diameter comprised between 1 and 5 microns,
0.3 g of mechano-structured biomaterial prepared in Example 3,
1 g of essential oils complex, qsp 100 g of demineralized water, white petroleum jelly and Shea butter.

The product in the form of cream was applied every 48 hours to a horse in the case of a necrosis of the breast 37 cm high and 16 cm wide, which had caused a loss of substance involving all of the skin covering as well as the sub-cutaneous cell tissue as far as the fascia of the underlying muscles. It was possible to note a reduction in the surface area and depth of the lesion at a rate of 1 cm a day and healing after 45 days without discoloration of the hair.

Example 13

A solution which can be injected by intravenous route for the treatment of cachexia and muscle atrophy is prepared, the composition of which for 20 ml is as follows:
  1 g of mechano-structured nacre of Example 2,
  qsp 20 ml of injectable isotonic solution.

The injectable preparation was administered once by intravenous route to a cachexic and malnourished horse undergoing treatment in a veterinary centre. After 15 days, the animal's weight increase was of the order of 25 kg.

Example 14

A material is prepared for filling losses of substances from the hoof in ungulates, such as sand cracks, seedy-toe and other disabling pathologies of the hoof. The composition per 100 g of the filling material is as follows:
  4 g of nacre powder having an mean volume diameter comprised between 10 and 20 microns,
  1 g of mechano-structured nacre of Example 2,
  4 g of beech sawdust,
  gel of single-phase neutral silicone qsp 100 g.

Example 15

An implant according to the invention is prepared as follows:
  the implant, as described in FIG. 1, is covered with mechano-structured nacre prepared in Example 2;
  after local and/or locoregional or general anaesthesia, the maxillary bone is exposed after incision or using a circular scalpel, perpendicular to the site to be implanted;
  the bone is drilled using calibrated instruments so as to provide a bony well with the dimensions of the implant which is inserted to the limit of the Dacron felt of the superstructure described in FIG. 1, overhanging the cortical bone;
  after suture of the gingival alveolar mucosa, the implant is left embedded without loading.

Clinical and radiological examination 2 weeks post-operatively show complete gingival cicatrization as well as rapid filling of the peri-implant space, by colonization of the blind pores of the implant surface by osteoblasts.

A biopsy at the level of the Dacron felt ring shows on a histological section, a colonization of the Dacron felt meshes by the fibroblasts, without the presence of inflammatory cells, producing a true gingival setting with gingiva attached.

Example 16

A bone substitute piece according to the invention is prepared as follows:
  the bone substitute piece, as described in FIGS. 2 and 3, is covered with mechano-structured nacre prepared in Example 2;
  after radiography and scanning of the zone to be operated on, then local and/or locoregional, or general anaesthesia, a transversal incision is made on the maxillary crest followed by detachment of the mucoperiosteum so as to allow the insertion of a silicone expander of similar shape and dimensions to the substitute piece. Progressive filling of the expander with physiological serum over approximately 3 weeks causes an expansion of the gingival alveolar mucosa;
  after removal of the expander, the substitute piece is inserted into the tunnel thus obtained and fixed using the fastening screw, its upper surface covered by the alveolar mucosa, the lower surface resting on the maxillary bone the surface of which has been roughened;
  the substitute piece is fixed to the fibrous tissue covered by mucous membrane by transverse sutures.

Radiological examinations after 4 weeks show complete integration of the piece and its fixing by the fibrous tissue covered by mucous membrane.

The invention claimed is:

1. A process for the preparation of mechano-structured, nanometric nacre powder comprising:
  providing a nacre particles obtained from the nacreous test of shells of bivalves, which is the inner layer of the bivalves, the nacre particles being in the form of a micrometric nacre powder; and
  treating the micrometric nacre powder by mechanosynthesis to obtain a modified, mechano-structured nacre in the form of nanometric size powder,
  the temperature of the nacre being below 40° C. during the whole process.

2. The process according to claim 1, wherein the micrometric nacre particles to be treated by mechanosynthesis are obtained from the nacreous test of bivalves selected from the group consisting of:
  *Pinctada maxima*, *Pinctada margaritifera* or other *Pinctadas*, *Tridacnae gigas*, and mixtures thereof.

3. The process according to claim 1, wherein the mechanosynthesis comprises the following successive stages:
  a) the micrometric nacre powder is placed in a grinding bowl of a planetary mill, then
  b) $N_i$ grinding beads of diameter $D_i$ are placed in the grinding bowl, i being an integer comprised between 1 and 20 and $N_i$ being an integer comprised between 2 and 150,
  c) the planetary mill is started up at a rotational speed V comprised between 800 and 1400 rpm, with an acceleration of 90 to 110 G,
  d) the planetary mill is stopped and the grinding beads of diameter $D_i$ are removed,
  stages b, c and d are repeated with $N_{i+1}$, with $N_{i+1} > N_i$, grinding beads of diameter $D_{i+1}$, with $D_{i+1} < D_i$, until a nacre powder having particles of a desired nanometric size is obtained;
  when the desired nanometric size of the particles is obtained, on completion of stage d), the mechano-structured nanometric nacre powder is recovered.

4. The process according to claim 3, wherein the planetary mill is started up at a rotational speed V of 1100 rpm, with an acceleration of 90 to 100 G.

5. The process according to claim 3, wherein the number of grinding beads and their diameters are such that there is a ratio of 2/5 by weight of nacre particles to be treated to 3/5 by weight of beads.

6. The process according to claim 3, wherein the grinding bowl, the nacre powder to be treated or the grinding beads are cooled down before use to a temperature comprised between −30° C. and 5° C.

7. The process according to claim 6, wherein the grinding bowl, the nacre powder to be treated or the grinding beads are further cooled down before each repetition of stages b), c) and d).

8. The process according to claim 3, wherein stage c) is carried out under a cooled atmosphere or interspersed with cooling cycles.

9. The process according to claim 1, wherein mechanosynthesis comprises:

the micrometric nacre powder to be treated is placed in a grinding bowl, grinding beads are placed in the grinding bowl and the assembly comprising the nacre powder to be treated, the grinding beads and the grinding bowl are cooled down to a temperature comprised between −30° C. and 5° C., the refrigerated nacre powder to be treated then undergoes:

a) grinding cycles with grinding beads 10 mm in diameter until nacre particles having an mean volume diameter comprised between 5 and 15 microns are obtained, then b) grinding cycles with grinding beads 5 mm in diameter, until nacre particles having an mean volume diameter comprised between 800 nm and 2 µm are obtained, then c) grinding cycles with grinding beads 2 mm in diameter, until nacre particles having an mean volume diameter of less than 500 nanometres are obtained, the mechano-structured nanometric nacre powder is then recovered.

10. The process according to claim 1, wherein mechanosynthesis comprises:

the micrometric nacre powder to be treated is placed in a grinding bowl, grinding beads are placed in the grinding bowl and the assembly comprising the nacre powder to be treated, the grinding beads and the grinding bowl is cooled down to a temperature comprised between −30° C. and 5° C., the refrigerated nacre powder then undergoes:

a) 5 to 15 grinding cycles, each cycle lasting 1 to 10 minutes, carried out with grinding beads 10 mm in diameter, then b) 5 to 15 grinding cycles, of 1 to 10 minutes, carried out with grinding beads 5 mm in diameter, then c) 5 to 15 grinding cycles, of 1 to 10 minutescarried out with grinding beads 2 mm in diameter, the mechano-structured nanometric nacre powder is then recovered.

11. The process according to claim 1, wherein the micrometric nacre powder to be treated by mechanosynthesis is ground together with at least one material other than the nacre.

12. The process according to claim 11, wherein the material is chosen from the group consisting of more than 90%-deacetylated chitosan powder, chitin, algae, insoluble and soluble biopolymers extracted from the nacreous test and from the outer shell of the abovementioned bivalves, copper sulphate ($CuSO_4$, $5H_2O$), zinc oxide, gold or silver, and mixtures thereof.

13. The process according to claim 1, wherein the temperature of the nacre is kept below 20° C.

14. The process according to claim 1, wherein the temperature of the nacre is kept below or equal to 0° C.

* * * * *